(12) United States Patent
Hall et al.

(10) Patent No.: US 8,830,481 B2
(45) Date of Patent: *Sep. 9, 2014

(54) POLARIZATION BASED INTERFEROMETRIC DETECTOR

(71) Applicant: Bioptix Diagnostics, Inc., Boulder, CO (US)

(72) Inventors: John Hall, Broomfield, CO (US); Viatcheslav Petropavlovskikh, Louisville, CO (US); Oyvind Nilsen, Boulder, CO (US)

(73) Assignee: Bioptix LLC, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/929,731

(22) Filed: Jun. 27, 2013

(65) Prior Publication Data

US 2013/0335741 A1    Dec. 19, 2013

Related U.S. Application Data

(63) Continuation of application No. 11/735,900, filed on Apr. 16, 2007, now Pat. No. 8,488,120, which is a continuation-in-part of application No. 11/379,026, filed on Apr. 17, 2006, now Pat. No. 7,233,396.

(51) Int. Cl.
    *G01B 9/02*   (2006.01)
    *G01N 21/25*  (2006.01)
    *G01N 21/41*  (2006.01)
    *G01N 21/21*  (2006.01)
    *G01N 21/55*  (2014.01)

(52) U.S. Cl.
    CPC .............. *G01N 21/21* (2013.01); *G01N 21/253* (2013.01); *G01N 21/41* (2013.01); *G01N 21/552* (2013.01); *G01N 21/553* (2013.01); *G01N 2021/212* (2013.01)
    USPC ........................................ 356/491

(58) Field of Classification Search
    USPC .......................... 356/364–370, 445, 450–521
    See application file for complete search history.

(56) References Cited

U.S. PATENT DOCUMENTS

| | | | |
|---|---|---|---|
| 5,600,441 A * | 2/1997 | de Groot et al. ............... | 356/492 |
| 5,615,009 A | 3/1997 | Sakura et al. | |

(Continued)

FOREIGN PATENT DOCUMENTS

| | | |
|---|---|---|
| JP | 09-304339 | 11/1997 |
| JP | 2001-041881 | 2/2001 |

(Continued)

OTHER PUBLICATIONS

Arwin, et al. Total Internal Reflection Ellipsometry: Principles and Applications. Appl. Opt. 2004; 43: 3028-3036.

(Continued)

*Primary Examiner* — Tarifur Chowdhury
*Assistant Examiner* — Michael P LaPage
(74) *Attorney, Agent, or Firm* — Wilson Sonsini Goodrich & Rosati

(57) ABSTRACT

A sensor and method for determining the optical properties of a sample material is disclosed. The sensor comprises a light source that generates a linearly polarized light beam having a predetermined polarization orientation with respect to the plane of incidence. The linearly polarized light beam is reflected off the sample and is split into second and third light beams where the second and third light beam consist of the combined projections of mutually orthogonal components of the first light beam. A signal processor measures the intensity difference between the second and third light beams to calculate the phase difference induced by the sample material.

37 Claims, 5 Drawing Sheets

(56) References Cited

U.S. PATENT DOCUMENTS

| | | | |
|---|---|---|---|
| 5,955,377 | A | 9/1999 | Maul et al. |
| 6,313,918 | B1 | 11/2001 | Hill |
| 6,515,745 | B2 | 2/2003 | Vurens et al. |
| 6,594,011 | B1 | 7/2003 | Kempen |
| 6,628,376 | B1 | 9/2003 | Nikitin et al. |
| 6,738,141 | B1 | 5/2004 | Thirstrup |
| 6,844,935 | B2 | 1/2005 | Lee et al. |
| 6,859,280 | B2 | 2/2005 | Kempen |
| 6,888,638 | B1 | 5/2005 | Hill |
| 6,970,249 | B1 | 11/2005 | Lipson et al. |
| 7,027,676 | B2 | 4/2006 | Van Wiggeren et al. |
| 7,233,396 | B1 | 6/2007 | Hall et al. |
| 7,339,681 | B2 | 3/2008 | Su et al. |
| 7,407,817 | B2 | 8/2008 | Ho et al. |
| 8,488,120 | B2 | 7/2013 | Hall et al. |
| 2002/0021443 | A1 | 2/2002 | Venkatasubbarao et al. |
| 2003/0112446 | A1 | 6/2003 | Miller et al. |
| 2003/0219809 | A1* | 11/2003 | Chen et al. .................... 435/6 |
| 2003/0234937 | A1* | 12/2003 | Akao et al. .................... 356/491 |
| 2005/0052655 | A1 | 3/2005 | Jones et al. |
| 2005/0168749 | A1 | 8/2005 | Ye et al. |
| 2005/0194523 | A1 | 9/2005 | Van Wiggeren et al. |
| 2005/0201717 | A1 | 9/2005 | Matsumura |
| 2006/0019313 | A1 | 1/2006 | Andersson et al. |
| 2006/0023221 | A1 | 2/2006 | Kimura |
| 2006/0082781 | A1* | 4/2006 | Chan et al. .................... 356/495 |
| 2006/0119859 | A1 | 6/2006 | Su et al. |
| 2006/0231762 | A1 | 10/2006 | Ohtake et al. |
| 2007/0008546 | A1 | 1/2007 | Ho et al. |
| 2007/0166763 | A1 | 7/2007 | Ho et al. |
| 2008/0002202 | A1 | 1/2008 | Hall et al. |
| 2008/0002212 | A1* | 1/2008 | Kawasaki et al. ............. 356/512 |
| 2008/0304072 | A1 | 12/2008 | Ho et al. |

FOREIGN PATENT DOCUMENTS

| | | |
|---|---|---|
| JP | 2002505425 | 2/2002 |
| JP | 2004-354246 | 12/2004 |
| JP | 2005-257458 | 9/2005 |
| JP | 2006064405 | 3/2006 |
| WO | WO 2004/090505 A2 | 10/2004 |

OTHER PUBLICATIONS

Attridge, et al. Sensitivity enhancement of optical immunosensors by the use of a surface plasmon resonance fluoroimmunoassay. Biosens Bioelectron. 1991;6(3):201-14.

Copper, et al. Label-free screening of bio-molecular interactions. Anal Bioanal Chem. Nov. 2003;377(5):834-42.

European search report and search opinion dated Aug. 10, 2011 for Application No. 07760723.2.

Ex Parte Quayle action dated Nov. 30, 2006 for U.S. Appl. No. 11/379,026.

Fang, et al. Determination of Ribonuclease H Surface Enzyme Kinetics by Surface Plasmon Resonance Imaging and Surface Plasmon Fluorescence Spectroscopy. Anal. Chem. 2005; 77:6528-6534.

Fattinger, et al. The difference interferometer: a highly sensitive optical probe for quantification of molecular surface concentration. Biosensors and Bioelectronics. 1993; 8(2):99-107.

Goodrich, et al. Direct Detection of Genomic DNA by Enzymatically Amplified SPR Imaging Measurements of RNA Microarrays. J. Am. Chem. Soc. 2004; 126:4086-4087.

Goodrich, et al. Enzymatically Amplified Surface Plasmon Resonance Imaging Method Using RNase H and RNA Microarrays for the Ultrasensitive Detection of Nucleic Acids. Anal. Chem. 2004: 76:6173-6178.

Guo, et al. Small-angle measurement based on surface-plasmon resonance and the use of magneto-optical modulation. Applied Optics. 1999; 38(31):6550-6555.

Hall, et al. Detection and discrimination of low concentration gas contaminants by means of interferometrically-sensed polymers. IEEE Sensors. 2005; 1366-1369.

Homola, et al. Surface plasmon resonance sensors: review. Sensors and Actuators. 1999; B 54:3-15.

International search report and written opinion dated Oct. 27, 2008 for PCT Application No. US2007/66723.

Kano, et al. Surface-plasmon sensor for absorption-sensitivity enhancement. Appl. Opt. 1994; 33:5166-5170.

Kruchinin, et al. Surface Plasmon resonance monitoring by means of polarization state measurement in reflected light as the basis of a DNA-probe biosensor. Sensors and Actuators. 1996; B 30:77-80.

Markov, et al. Label-free molecular interaction determinations with nanoscale interferometry. Label-free molecular interaction determinations with nanoscale interferometry.

Nikitin, et al. Bio-optoelectronical "tongue" for detection of pesticide contamination of water. Transducers'97. 1997 International Conference on Solid-State Sensors and Actuators, Chicago, Jun. 16-19, 1997. pp. 495-497.

Office action dated Feb. 1, 2012 for U.S. Appl. No. 11/735,900.
Office action dated Feb. 23, 2011 for U.S. Appl. No. 11/735,900.
Office action dated Aug. 1, 2011 for U.S. Appl. No. 11/735,900.
Office action dated Sep. 7, 2010 for U.S. Appl. No. 11/735,900.
Office action dated Oct. 2, 2012 for U.S. Appl. No. 11/735,900.
Office action dated Dec. 4, 2009 for U.S. Appl. No. 11/735,900.

Shen, et al. Optical phase-shift detection of surface plasmon resonance. Applied Optics. 1998; 37(10):1747-1751.

Wu, et al. Highly sensitive differential phase-sensitive surface plasmon resonance biosensor based on the Mach-Zehnder configuration. Optics Letters. 2004; 29(20):2378-2380.

Wu, et al. Sensitivity-tunable optical sensors based on surface plasmon resonance and phase detection. Optics Express. 2004; 12(15):3509-3514.

Yu, et al. A surface plasmon resonance imaging Interferometry for protein micro-array detection. Sensors and Actuators. 2005; B 108 :765-771.

Zhu, X.D. Comparison of two optical techniques for label-free detection of biomolecular microarrays on solids. Optics Communications. 2006; 259:751-753.

Nikitin, et al. Spectral-phase interference method for detecting biochemical reactions on a surface. Quantum electronics. 2000; 30(12):1099-1104.

* cited by examiner

POLARIZATION BASED INTERFEROMETRIC DETECTOR

CROSS-REFERENCE

This application is a continuation application of U.S. patent application Ser. No. 11/735,900, filed on Apr. 16, 2007 which is a continuation-in-part application of U.S. patent application Ser. No. 11/379,026, filed Apr. 17, 2006, now U.S. Pat. No. 7,233,396 which are all incorporated herein by reference in their entirety.

FIELD ON THE INVENTION

This invention relates to affinity bio- and chemical sensors and is based on measurement of the phase shift between two orthogonal polarization components for quantitative analysis of liquid and gaseous samples.

BACKGROUND OF THE INVENTION

Scientists and industry alike are continually seeking methods to evaluate molecular interactions and eliminate the uncertainty associated with utilizing labels to detect the location of molecules of interest. Label-free technologies are crucial in terms of addressing this issue, as these techniques allow researchers to look at molecular systems without perturbing them with extraneous chemistries that fundamentally change the dynamics of interaction. The sensitivity of instruments designed to analyze these molecular interactions is of paramount concern because often molecules of interest are difficult and expensive to produce and/or isolate, or are present in biological samples only at very low concentrations. Compounding the issue of miniscule quantities are the numerous variations of analytes, such as in drug development's combinatorial chemistry libraries of which binding characteristics are desired. It is desirable to develop sensors capable of integration with high throughput screening methods. It must also be sensitive enough to detect precious amounts of interesting molecules, quickly and specifically.

SUMMARY OF THE INVENTION

A system comprising a light source, a sensor, an optical retarder, a beam splitter, and a detector for determining the optical properties of a sample material is disclosed. The system comprises a light source for generating a first light beam having first and second lightwaves, the first lightwave having a first linear polarization and the second lightwave having a second linear polarization, the first and second linear polarizations being orthogonal to each other, and the first and second lightwaves being in phase relative to each other. The first linear polarization (p-polarization) being in the plane of incidence, and the second linear polarization (s-polarization) being normal to the plane of incidence. The intensity of the first lightwave and second lightwave are set to a predetermined ratio. The system also includes an optical retarder for providing a variable phase shift between the first and second lightwaves by imposing a relative delay between the first and the second lightwaves and a prism interface for reflecting the first light beam from the sample material under Total Internal Reflection (TIR) or Frustrated Total Internal Reflection (FTR) conditions.

A polarizing beam splitter is used for splitting the first light beam into a second light beam and a third light beam after the first light beam is reflected from the optical interface, where the second light beam and the third light beam comprise combined projections of mutually orthogonal polarization components on the main axes of the beam splitter. A signal processor measures the intensity difference between the second and the third light beams to calculate the phase difference induced by the sample material, the signal processor receiving a first intensity measurement from a first detector and a second intensity measurement from a second detector where the first and second detectors measure the intensities of the second and third light beams, respectively.

The light source for the system may comprise a coherent light beam that is linearly polarized and with the linear polarization rotated at a predetermined angle with respect to the plane of the sensor surface. The incident angle is determined based on maximum phase shift between the first and second lightwaves due to a change on the sensor surface. The light source may be a gas laser, a diode pumped solid state laser, an excimer lamp, a vertical cavity surface emitting laser, a laser diode, or any light source that will provide a linearly polarized coherent light having a wavelength range of about 500-700 nanometers.

The polarizing beam splitter may be oriented such that the intensity of the second and third lightbeams are substantially equal or equal to one another. The polarizing beam splitter may be oriented at about a 45 degree angle to the plane of the optical interface.

The predetermined ratio of the intensities of the first and second lightwaves is β where:

$$\beta = \frac{I_P^0}{I_P^1} = \frac{I_P^0}{I_S^0},$$

and where $I^0_P$ and $I^1_P$ are intensities of the first lightwave before and after reflection from the sample material, respectively, and $I^0_S$ is the intensity of the second lightwave.

The optical retarder in the system may be a Fresnel rhomb prism or a right angle prism to provide a substantially 90 degree phase shift between orthogonal polarization components.

The system may further comprise one or more optical components located in the path of the first beam where the one or more optical components convert substantially elliptical polarization into substantially circular polarization before the light beam is transmitted to the beam splitter.

The system comprises at least one sensor and may comprise at least one SPR transducer. The sensor may contain sensing material comprising biological molecules, such as antibodies, antigens, oligonucleotides, proteins, enzymes, receptors, receptor ligands, organic molecules, and catalysts. Alternatively sample material may be applied to an array of transducers, each transducer containing sensing material, with subsequent analysis by the sensor. The sample material may comprise nucleic acid, proteins, polypeptides, organic molecules, bacteria and viral particles.

The system of the invention is capable of detecting surface refractive index change of at least $5 \times 10^{-8}$ Refractive Index Units. The system is capable of detecting amounts of sample of at least 50 femtograms or at least 2,230,000 molecules of a 100 amino acid peptide, when associated with the molecularly-specific surface.

In another aspect of the present invention a method is provided of determining the optical properties of a sample material. The method comprises steps of applying the sample material to an optical interface of a transducer containing sensing material, generating a first light beam having first and second lightwaves, the first lightwave having a first linear polarization and the second lightwave having a second linear polarization, the first and second linear polarizations being orthogonal to each other. A substantially 90 degree phase shift between the first and second lightwaves, after the first light beam is reflected from the sensor surface, is provided by imposing a relative delay between the first and the second lightwaves. The first light beam reflects from the sample material under TIR or FTR conditions, whereupon the first light beam is split into a second light beam and a third light beam after the providing and the reflecting steps, where the second light beam and the third light beam comprise or consist of combined projections of mutually orthogonal polarization components of the first light beam. The intensity difference is measured between the second and the third light beams to calculate the phase difference induced by the sample material.

In yet another aspect of the invention, a method is provided to detect the presence of analyte in a sample, comprising the steps of applying the sample to an optical interface of a transducer containing sensing material; reflecting a first light beam off the optical interface, wherein the first light beam has a first and a second lightwave; splitting the first light beam after it is reflected from the optical interface into a second light beam and a third light beam; and measuring the difference in intensities between the second and the third light beams to calculate a phase difference induced by the sample.

In the methods of the invention, the first light beam may be linearly polarized and coherent. The first light beam may have first and second lightwaves. The first lightwave may have a first linear polarization and the second lightwave may have a second linear polarization. The first and second linear polarizations are orthogonal to each other. The first light beam, after being reflected from the sensor surface, may be substantially elliptically polarized and may be converted into substantially circular polarized light prior to splitting the first light beam into the second and third light beam. A 90 degree or substantially 90 degree phase shift is provided by reflecting the first light beam from two reflection surfaces under total internal reflection conditions, and/or by means of adjusting optical retarder in the path of the first light beam.

In the methods of the invention, the predetermined ratio of the intensities of the first and second lightwaves is $\beta$ where:

$$\beta = \frac{I_P^0}{I_P^1} = \frac{I_P^0}{I_S^0},$$

and where $I_P^0$ and $I_P^1$ are intensities of the first lightwave before and after reflection from the sample material, respectively, and $I_S^0$ is the intensity of the second lightwave.

In some cases the intensity of the second and third light beams may be equal or substantially equal. The second and the third light beams may consist of combined projections of mutually orthogonal polarization components on the main axes of a beam splitter.

The systems herein can include sensing material immobilized on the optical interface. Such material can comprise e.g., biological molecules, such as antibodies, antigens, oligonucleotides, proteins, enzymes, receptors, receptor ligands, organic molecules, and catalysts. The sample material may comprise nucleic acid, proteins, polypeptides, organic molecules, bacteria and viral particles. Sample material may be applied to one transducer or to an array of transducers, each transducer containing sensing material, with subsequent analysis by the sensor.

The methods of the invention are capable of detecting surface refractive index change of at least $5\times10^{-8}$ Refractive Index Units (RIU) and of detecting amounts of sample of at least 50 femtograms or at least 2,230,000 molecules of a 100 amino acid peptide, when associated with the molecularly-specific surface. The analysis may be performed in the presence of a reference sample, with or without analyte present, and with or without analyte of known identity and amount present in the reference sample.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
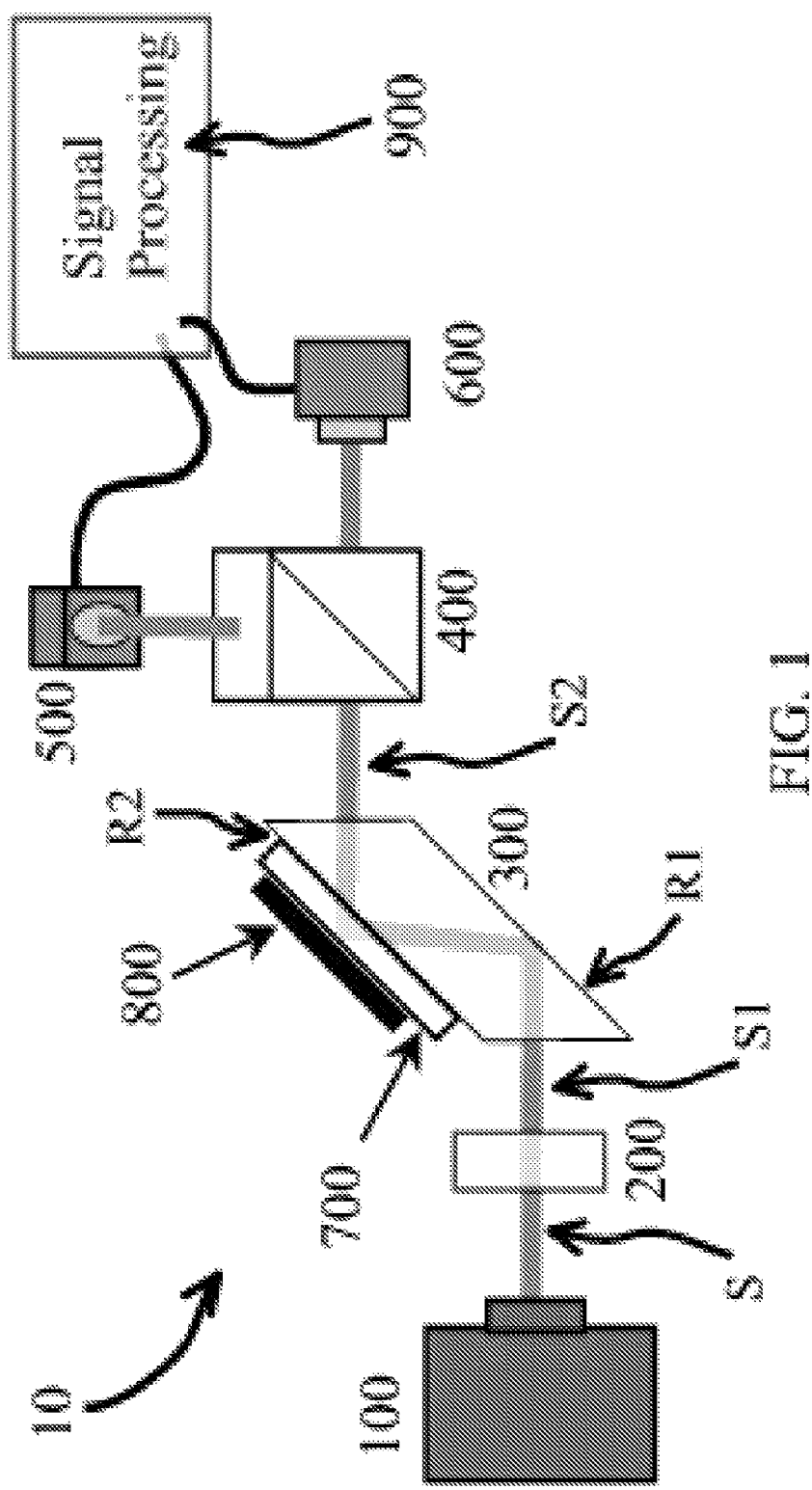
FIG. 1 illustrates the TIR sensor using the Fresnel rhomb approach in accordance with an embodiment of the present invention.

Optical sensors based on the detection of analyte binding to thin receptor films at the sensor surface have been studied intensively. The use of an optical Total Internal Reflection (TIR) configuration for measurement of index of refraction changes in the evanescent field is common to interferometers, ellipsometers and polariscopes. All these techniques can be applied to the measurements of chemical or biological layered media, with the goal of label free detection.

Internal reflection ellipsometry (IRE) may be used for orientation of liquid crystals and absorption of solutes onto substrate surfaces and for measurements of the refractive index of liquids. Measurements were conducted in the total internal reflection region of the incident angle that is not favorable for thickness measurements owing to low sensitivity. In an effort to enhance the sensitivity of such thickness measurements, the implementation of the Surface Plasmon Resonance (SPR) effect has been developed—a method falling under the more general Frustrated Total Internal Reflection (FTR) approach. However, there remains a need for highly sensitive devices for measurements of both thickness and index of refraction changes in bio- and chemical sensing devices.

Several methods have been employed to measure the spatial reflection coefficients and overall intensity from the sensor interface. These intensity-based techniques suffer from the fluctuation of intensity in light sources and the relatively small-reflected coefficient from the sensor surface. Higher detection sensitivity is always desirable for improving sensing performance. High sensitivity may be achieved utilizing other factors. It has been found that a lightwave's phase can change much more abruptly than the intensity when the refractive index or thickness of a binding layer on the surface has been changed. Several methods may be employed in sensors by measuring the phase change from the sensor interface during SPR, even with the capability of sensor array imaging. For example, a sensor based on the combination of SPR and heterodyne interferometry with extremely high sensitivity and low-noise was proposed.

During both TIR and FTR conditions the phase difference between p- and s-polarized components of reflected beam experiences a rapid shift whenever the optical properties of an adjacent medium change, such as refractive index or thickness of the affinity sensitive layer. Moreover measurement of the phase shift of the p-polarized component of the incident beam yields significantly higher sensitivity than SPR techniques that measure intensity associated with incident angle change. Furthermore, the phase-change method allows using both metal coated and optically transparent transducers without a special metallic coating.

The method disclosed herein applies in a similar manner to both TIR and FTR conditions in terms of measured parameters and general configuration of the system. Utilizing the SPR phenomena in sensing applications has been demonstrated in several different configurations. A common approach uses the Kretschman configuration. A coherent p-polarized optical wave is reflected under TIR conditions on an interface between an optically dense material, such as a glass prism, and a rarefied medium, which in this case is the sample medium, whose index of refraction is lower than the dense medium. The interface between the two media is coated with a thin conductive metal film, which acts as an absorber for the optical wave. When specific conditions dependent on the light wave's angle of incidence, wavelength and the media's refractive indices are met, the optical wave causes the metal's surface plasmon electrons to oscillate at resonance, absorbing the wave's energy in the metal film. During these resonance conditions, variations in the sample's index of refraction will produce sharp changes to the optical phase of the p-polarized component, while the s-polarization phase remains relatively constant. At the resonant conditions, most of the p-polarization light component in contrast to TIR condition is absorbed in the metal film via the SPR effect. This fact is exploited by intensity based SPR sensors and ellipsometers, relating the conditions of the intensity minimum of the reflected light to the optical configuration to thereby deduce the sample's index of refraction or layer thickness.

The described approach uses a single light beam configuration and monitors any changes in the layered media by observing the intensity of orthogonal polarization components (i.e. p- and s-polarizations, the p-polarization being in the plane of incidence and the s-polarization being normal to the plane of incidence), contained within this beam, reflected from the interacting TIR/SPR surface, and where the beam's polarization components experience intensity and phase shifts, the observation of which is optimized through obtaining a substantially 90° phase shift between the polarizations in the steady state sensor condition.

The method herein makes use of Polarization Based Interferometry (PBI) coupled with Total Internal Reflection (TIR) or Frustrated Total Internal Reflection (FTR) conditions to enable a level of sensitivity previously unattainable by other competing technologies. Interferometric measurement of two polarization states (s-polarization and p-polarization) of the same beam in combination with FTR elevates the sensitivity to surface refractive index change to at least $5 \times 10^{-8}$ Refractive Index Units (RIU), which permits detection of at least 50 femtograms of sample, or at least 2,230,000 molecules of a 100 amino acid peptide, when associated with the molecularly-specific surface.

The present method is applied under either TIR or FTR conditions. The phase difference between p- and s-polarization components of incident beam experiences a rapid shift when dielectric properties of the medium adjacent to the transducer surface change. The phase of the p-polarization component changes much more abruptly than the intensity when the refractive index or thickness of a binding layer on the surface has been changed. This difference allows the use of a single substantially linearly polarized beam tilted under a certain adjustable angle for sensitive detection of refractive index change, on or in close vicinity to, the transducer surface. The highest sensitivity is achieved when the two components are in phase-quadrature or 90° out of phase. The combination of obtaining orthogonal polarization components with a polarizing beam splitter and differential signal processing scheme provides direct, highly sensitive measurement of small phase shifts and multiplex array imaging detection.

The present invention provides a method for evaluation of multiple complementary chemistries in an array format that enables high throughput screening at high sensitivity level. Potential uses for such a device are infectious disease screening in blood and detection of virus or bacterial particles in air, pharmacokinetic research and primary binding studies for drug development applications in addition to personalized medicine, particularly for cancer, detection of bio- and chemical warfare agents/hazards, and quality control for industrial processes.

Some examples of infectious disease screening may include; identification of whole bacteria, whole virus or viral particles, whole infectious parasites or other lifecycle congeners thereof; identification of antibodies raised against specific bacterial or viral strains; excreted/secreted antigens or nucleic acid markers from infectious agents; or protein biomarkers of disease either from the host or disease causing agent. Infectious disease screening could be use for either diagnostic purposes or for blood supply safety monitoring. Personalized medicine may use identification of antibodies, proteins, peptides, nucleic acids, and small organic molecules which arise from the disease state of interest. In pharmaceutical research and development, the present invention may be used in screening of nucleic acids, antibodies, proteins, peptides and synthetic organic molecules to identify active molecules suitable for development as a drug candidate; detection of drug candidates in biological samples throughout preclinical and clinical development; and safety monitoring of subjects in clinical and community settings, for detection and quantification.

Other potential uses may include air and water quality monitoring. Monitoring can be for particulates, pollutants, toxins, industrial waste products, waste biologics, or inorganic health hazards.

FIG. 1 shows an optical TIR sensor 10 with an embodiment of the proposed invention. Sensor 10 comprises a light source 100, a half-wave plate 200, a Fresnel rhomb 300, a polarized beam splitter 400, two photo detectors 500 and 600, and a slide containing a specific sensor material 700 which interacts with the sample 800.

Light source 100 can be any light source that provides substantially monochromatic coherent radiation, such as a laser. Preferably, the light source is a gas laser, a diode pumped solid state laser, an excimer lamp, vertical cavity surface emitting laser or a laser diode. Preferably, light source 100 is any light source that will provide substantially monochromatic coherent radiation in the 500-700 nanometer wavelength range. Light source 100 is used to generate a substantially linearly polarized light beam S. Half-wave plate 200 is used to rotate the polarization of light beam S and to provide orientations of the polarization of the beam S at 45 degrees off the vertical axis. As a result signal S1 contains both s- and p-polarization components where the phase difference between the s- and p-polarization is zero degrees.

Fresnel rhomb 300 is used to introduce a substantially 90 degree phase difference between the s- and p-polarization components of signal S1. Other known methods of introducing a 90 degree phase shift between the s- and p-polarization components of signal S1 are also contemplated by the present invention. A slide 700 containing a specific sensor material is placed on one of the Fresnel rhomb surfaces, either R1 or R2 or both. Preferably, slide 700 is made of a material that is substantially transparent to the wavelengths of light source 100. Preferably, slide 700 is made of a material that has a higher index of refraction than the sample. Preferably, slide 700 is made of glass, plastic, silicon or ceramic. The sensor material in slide 700 interacts with the sample 800. This interaction produces a phase shift between the s- and p-polarization components when signal S1 reflects from the rhomb/slide boundary. Slide 700 and sample 800 are optically coupled to the rhomb 300 to ensure minimal losses and to maintain total internal reflection conditions.

Alternatively, slide 700 and prism 300 are part of a single assembly thereby eliminating the need to use index matching fluid. In one embodiment, the angle of incidence of the light beam from light source 100 maybe varied around the optimum TIR/FTR angle for a particular application. The incident angle is determined based on the maximum phase shift between the first and second lightwaves due to a change on the sensor surface. The exact value of the incidence angle may be determined from the condition of yielding maximum sensitivity of the sensor and approximate linearity of the instrument response within a desired dynamic range even if the operating conditions change, i.e. new chip, variation in refractive of the metal or bio-coating, etc. In this embodiment, the signal that changes proportionally with the incident angle will be modulated at that frequency. Then the jittering frequency will be filtered out and will not affect the measured DC signal. Preferably, the frequency is significantly higher than the characteristic time of the measured process.

Polarized beam splitter 400 is used to combine the projections of the s- and p-polarized components of signal S2. Beam splitter 400 can be any beam splitter that combines the orthogonal polarization components. In some embodiments, beam splitter 400 is a cube beam splitter. The separated projections of the s- and p-polarization components are detected by detectors 500 and 600. Detectors 500 and 600 are any photo-detectors that accept an optical signal and generate an electrical signal containing the same information as the optical signal, e.g. a photodiode (PD) or a charge coupled device (CCD).

The electrical signals generated by detectors 500 and 600 are transmitted to a signal processing unit 900. The signal processing unit 900 reads the difference between the powers on the two detectors. This difference is directly proportional to the phase shift between the s- and p-polarization components. The phase shift between the s- and p-polarization components is indicative of changes in the optical properties, e.g. index of refraction or thickness of sensor material on slide 700.

Figure 2:
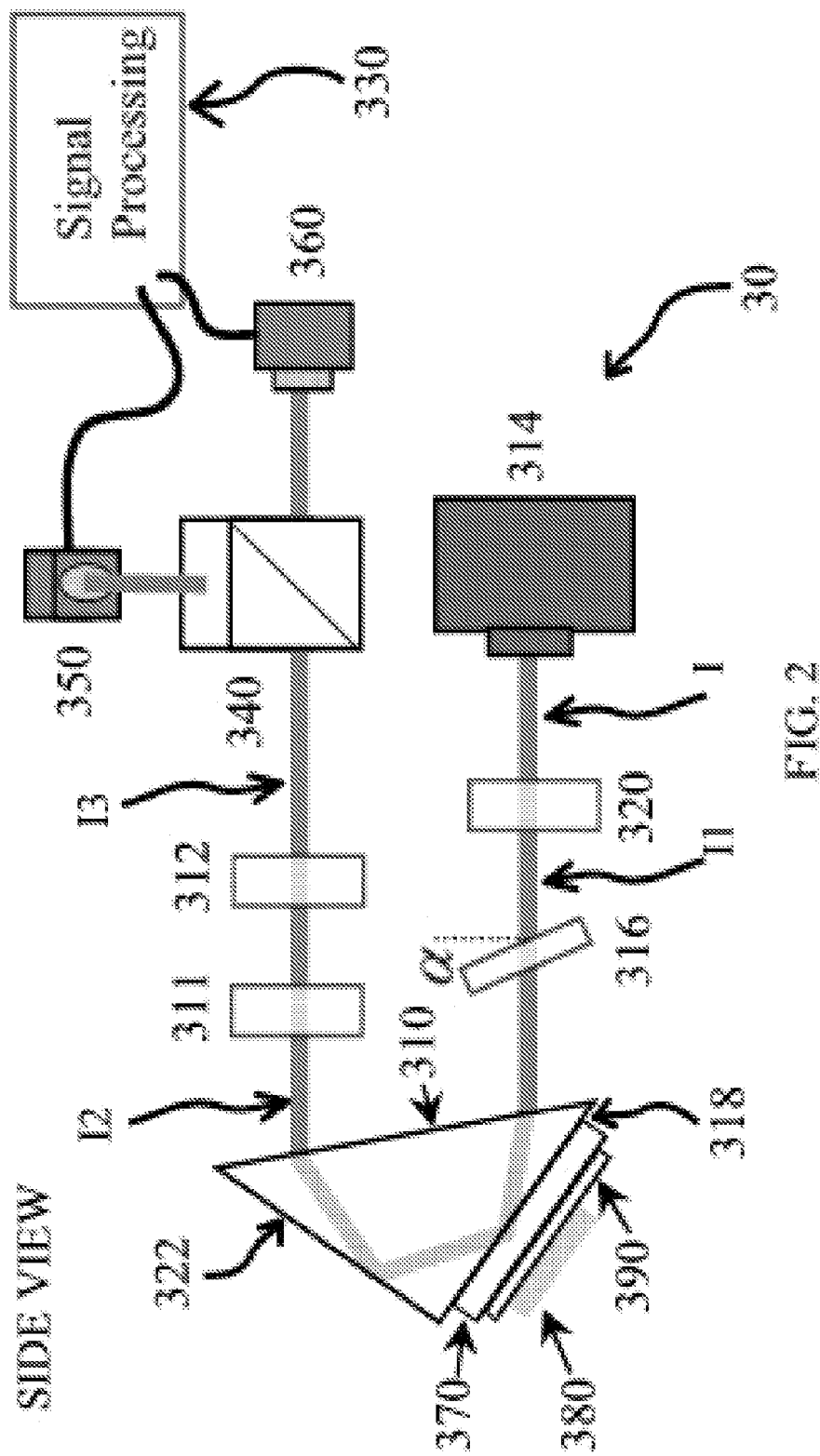
FIG. 2 shows an embodiment of the present invention using a right angle prism configuration.

FIG. 2 shows a sensor system 30 in accordance with an embodiment of the present invention. Sensor system 30 comprises a linear polarized light source 314, a half-wave plate 320, a right angle prism 310, a polarized beam splitter 340, and detectors 350 and 360. Light source 314 can be any light source that provides substantially monochromatic coherent radiation, such as a laser. In some embodiments, the light source is a gas laser, a diode pumped solid state laser, an excimer lamp, vertical cavity surface emitting laser or a laser diode. In some embodiments, light source 100 is any light source that will provide substantially monochromatic coherent radiation in the 532-680 nanometer wavelength range. Preferably, light source 314 is a tunable laser that provides a range of wavelengths. Light source 314 is used to generate a substantially linearly polarized optical beam I. Half-wave plate 320 is used to rotate the polarization of optical signal I by 45 degrees to generate signal I1. Half-wave plate 320 can also be used to adjust the relative optical power between the s- and p-polarizations at the TIR/SPR sensing surface, for signal optimization in accordance with equation (13) below. Beam I1 contains both s- and p-polarization components with a zero degree phase difference between them.

Beam I1 is sent to prism 310 where it attains elliptical polarization. The sensor system 30 also includes a host glass substrate 370, a metal film 390 with a bio-affinity coating applied, which interacts with the sample 380. Preferably, metal film 390 is a gold film. The right angle prism 310 may be rotated to accommodate for liquid or gas operation, or a different wavelength light source. Beam I1 experiences TIR condition at surface 318 of the prism, bounces off the second TIR surface 322 within the prism and exits the prism as beam I2. Beam I2 is elliptically polarized. Waveplates 311, 312 are used to achieve a beam I3 having substantially circular polarization (substantially 90 degree phase shift). In some embodiments, one of the wave plates is fixed with its fast axis at 45 degrees with respect to the plane of incidence. Optionally, wave plate 316 is used to obtain a substantially 90 degree phase difference. Both of these methods can be applied when the range of index of refraction for measured sample buffers is too broad and substantially 90 degree phase can not be achieved by the TIR reflections in the prism alone. Polarizing beam splitter 340 combines the projections of s- and p-polarization components of beam I3. Beam splitter 340 can be any beam splitter that combines the orthogonal polarization components of a single beam. Preferably beam splitter 340 is a cube beam splitter.

The combined projections of the s- and p-polarization components are detected by their respective detectors 350 and 360. Detectors 350 and 360 are any photo-detectors that accept an optical signal and generate an electrical signal containing the same information as the optical signal such as a photodiode (PD) or a charge coupled device (CCD). The electrical signals generated by detectors 350 and 360 are transmitted to a signal processing unit 330. The signal processing unit 330 reads the difference between the powers on the two detectors. This difference is directly proportional to the phase shift between the s- and p-polarization components. The phase shift between the s- and p-polarization components is indicative of changes in the optical properties, e.g. index of refraction or thickness of sensor material on metal film 390.

Optionally prism 310 may be rotated to accommodate different types of samples. During operation, if the sample reference leads to a significant change in the initial critical SPR angle, optimum operation might require a rotation of the prism 310. Optionally, the prism 310 may be dynamically rotated during a measurement. The shown configuration lets the input and output light beams from the prism 310 remain parallel even if the prism is rotated, thus additional dynamic alignment during operation is avoided.

The method of the present invention exploits the fact that the polarization state or the relative phase between s- and p-polarizations and the intensity of each individual polarization component, changes when the ratio of indices of refraction at an optical interface changes under total internal reflection (TIR) or frustrated total internal reflection (FTR) conditions. The method of the present invention seeks to extract the maximum possible difference between the changing s- and p-polarization components by imposing a substantially 90 degree phase shift between these components.

For pure TIR conditions the optical phase shift ($\delta$) between the p- and s-polarization components is expressed as:

$$\delta = \delta_P - \delta_S = 2 \cdot \tan^{-1}\left[\frac{\cos\theta_i \sqrt{\sin^2\theta_i - n_2^2/n_1^2}}{\sin^2\theta_i}\right] \quad (1)$$

Where $\theta_i$ is the light beam incident angle on the specific TIR/FTR interface, $n_2$ and $n_1$, the refractive indices of the sample medium and the prism 310, respectively. The incident angle may be fixed for a given instrument, with a built in static gain compensation system for simple systems, or variable, so as to accommodate for a range of buffer solution and SPR conditions, in order to achieve the highest possible sensitivity in more complex sensor systems.

For SPR, the reflection coefficients of the s- and p-polarizations can be written:

$$r_P = |r_P|e^{i\delta_P}, \quad r_S = |r_S|e^{i\delta_S} \quad (2)$$

And the phase difference between the p- and s-polarization components is:

$$\delta = \delta_P - \delta_S \quad (3)$$

which can be found from the overall complex reflection relation (2).

In general the substantially linear polarized beam incident on the sensing surface turns into elliptically polarized light when exiting the prism 310. The beam's electromagnetic vector is described by:

$$E_S = a_1 \cdot \cos(\tau + \delta_S) \quad (4)$$

$$E_P = a_2 \cdot \cos(\tau + \delta_P) \quad (5)$$

Where $\delta_1$ and $\delta_2$ are the phase shifts for the s- and p-polarizations respectively, and:

$$\tau = \omega t - \vec{k} \cdot \vec{r} \quad (6)$$

If two detectors $D_1$ and $D_2$ are located orthogonally and turned by angle $\Psi$ in respect to the plane of incidence, one can obtain the difference in power between them as such:

$$D_2 - D_1 = \Delta I = \tfrac{1}{2}(a_1^2 - a_2^2)\cos 2\Psi + a_1 a_2 \sin 2\Psi \cos \delta \quad (7)$$

If detectors are located at angle $\Psi$ such as $$\tan 2\Psi^* = \frac{a_2^2 - a_1^2}{2a_1 a_2 \cos\delta},$$

then $D_1 - D_2 = 0$.

Assuming now that the following assumptions hold:

$$a_2 = a_{20} + \Delta a_2, \quad \frac{\Delta a_2}{a_{20}} \ll 1 \quad (8)$$

$$\delta = \delta_0 + \Delta\delta, \quad \frac{\Delta\delta}{\delta_0} \ll 1 \quad (9)$$

Here $a_{20}$ and $\delta_0$ refer to initial or steady state conditions. From this, it follows:

$$\Delta I\big|_0 = \frac{1}{2}(a_1^2 - a_{20}^2)\cos 2\Psi + a_1 a_{20}\sin 2\Psi \cos\delta_0 \quad (10)$$

$$\Delta I\big|_{a_2,\delta} \approx \quad (11)$$
$$\frac{1}{2}\cos 2\Psi(a_1^2 - a_{20}^2 + 2a_{20}\Delta a_2) + a_1(a_{20} + \Delta a_2)\sin 2\Psi \cos(\delta_0 + \Delta\delta)$$

The change in the differential intensity due to a change on the transducer surface therefore is:

$$R = [\Delta a_2(a_1 \sin 2\Psi \cos \delta_0 - a_{20} \cos 2\Psi)] - \{a_1 a_{20} \sin 2\Psi \sin \delta_0 \sin \Delta\delta\} \quad (12)$$

In equation (12) the first bracket refers to the "intensity" contribution, whereas the second bracket corresponds to the "phase" contribution of the response R. During TIR the intensity does not change and only the phase shifts. However both intensity and the phase change during SPR event. Nevertheless it was shown that the intensity contribution can be neglected, thus the sensor response is simplified to:

$$R = -a_1 a_{20} \sin 2\Psi \sin \delta_0 \sin \Delta\delta \quad (13)$$

A key concept of the mentioned approach is to maximize the response to phase changes.

The phase shift contribution is maximized when these conditions are met:

$$\sin 2\Psi \to 1 \Rightarrow \Psi \to \frac{\pi}{4} \quad (14)$$

$$\sin \delta_0 \to 1 \Rightarrow \delta_0 \to \frac{\pi}{2} \quad (15)$$

$$a_{20} = a_1 \quad (16)$$

The condition (15) refers to the phase quadrature or substantially 90° phase shift, as previously described. Condition (14) indicates that the detector should be located 45° off the plane of incidence. The conditions (14) and (16) can be also satisfied by rotating the half-wave plate located before the sensing prism to compensate for absorption of p-polarized component of the beam at the metal surface during SPR event. The rotation angle $\eta$ can be given as:

$$\tan\eta = \beta = \frac{I_P^0}{I_P^1} = \frac{I_P^0}{I_S^0}, \quad (17)$$

where $I^0_P$ and $I^1_P$ are intensity of p-polarization component before and after reflection from sensed surface, and $I^0_S$ is the intensity of the s-polarized component.

Finally, the maximum response that corresponds to circular polarization and is presented as:

$$R = -a_1^2 \sin \Delta\delta = I_0 \sin \Delta\delta \quad (18)$$

To obtain the desired phase difference of substantially 90° various methods of phase retardation can be used in the beam path. Specific examples to achieve the desired phase shift could be implemented by varying the following parameters: the prism 310 index of refraction, the index ratio on any non-sensor TIR/FTR interfaces within the prism, the incident angle $\theta_i$, and the number of TIR/FTR reflections within the prism.

For instance, a variable wave plate is a z-cut birefringent material, such as crystal quartz. The wave plate is designed such that the index of refraction varies with the tilting angle α, with respect to the optical axis, in a range between $n_o$ and $n_e$, where:

$$n_e = \sqrt{n_o^2 \cos^2\alpha + n_e^2 \sin^2\alpha}$$

The wave plate has an index of refraction of $n_o$ when positioned perpendicular to the beam, α=0, and a value of $n_e$ when aligned parallel to the beam. Therefore one can adjust the phase to be substantially 90° at the polarizing beam splitter 340 independent of what phase difference comes from the SPR at the metal film 390.

In addition, should the polarization not be completely circular, but a compressed vertical or horizontal ellipse (still substantially 90° phase shift between s and p), a half wave plate may be placed in front of the prism to balance the power of the two polarization components after the interaction at the sensing surface, creating the desired circular polarization.

Yet another way to achieve circular polarization is by the use of a liquid crystal polarization rotator that gives an easy way to control the polarization angle in response to a signal reading. For example, an applied voltage can be adjusted with a feed-back loop to provide a close to zero differential reading between the two polarization components.

Thus, various methods can be used to obtain the maximum output signal and phase difference quadrature. For instance, one can use two or more reflection surfaces to provide a substantially 90° phase shift between the two polarization components. This can be achieved by design of a special prism with proper refractive index that provides TIR conditions upon every reflection. With the SPR approach, a specially designed prism with two or more reflections can be used to provide a substantially 90° phase shift between s- and p-polarization. If the range of index of refraction for any intended sample buffer is too broad, substantially 90° phase shift may not be achieved without the use of the variable wave plate 316. In addition, two λ/4 wave plates (311, 312) may be placed after the prism 310, to convert the elliptically polarized beam to a circularly polarized beam, thus obtaining a substantially 90° phase shift.

Figure 3:
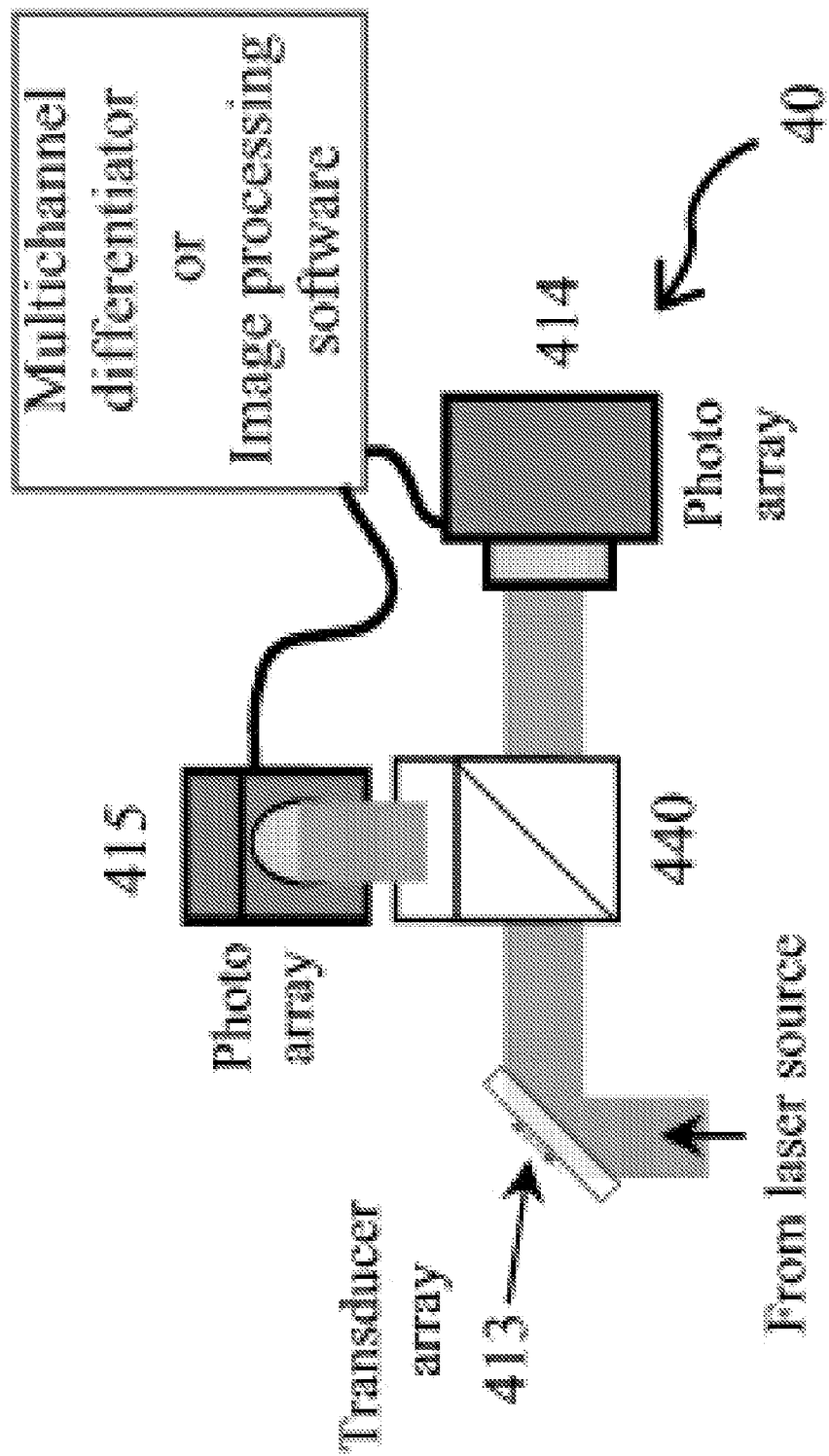
FIG. 3 shows a sensor array in accordance with an embodiment of the invention.
Figure 4:
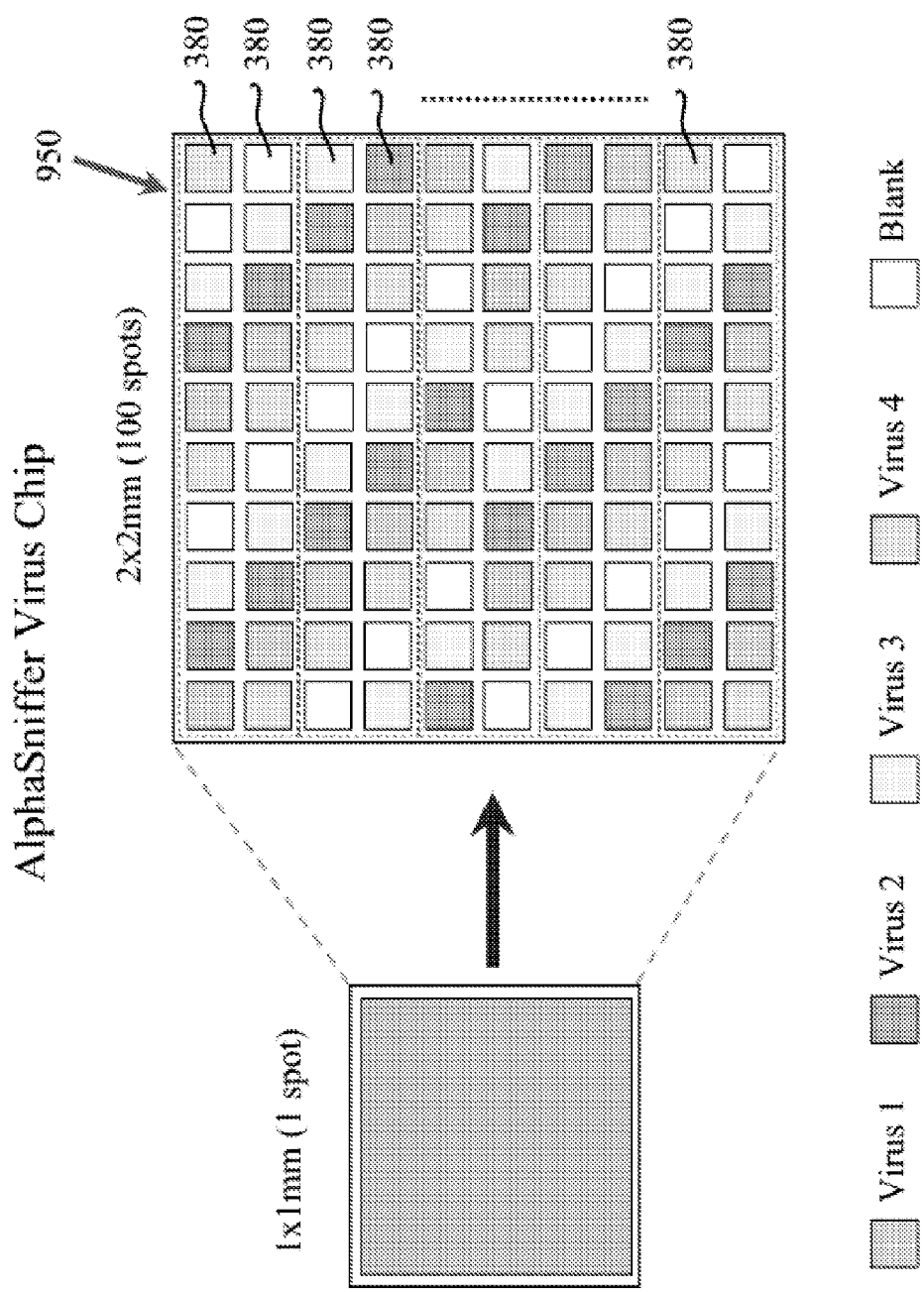
FIG. 4 shows a bio-sensor array chip for sensing applications that may operate in accordance with the invention.

FIG. 3 illustrates an embodiment of the present invention where the sample 413 is an array of sample transducers such as the AlphaSniffer virus chip 950 shown in FIG. 4. A chip 950 is illustrated in FIG. 4. The virus chip 950 in FIG. 4 can be on any substrate that is substantially transparent to light source 100 (FIG. 1) or 314 (FIG. 2). In one embodiment, chip 950 is on a glass or an SF11 substrate. Chip 950 has properties similar to other Lab-on-Chip or Bio-Chip approaches. In one embodiment, chip 950 can have open "affinity sensing features" on the surface exposed to analyzed liquid or the fluidics channel can be built as a part of the chip assembly. The fluid path can be a single channel or multi-channel. It's preferable to have a carrier stream (buffer). Preferably, the sample is degassed prior to delivery to the chip to avoid gas bubble formation on or in close vicinity of the chip surface FIG. 3 shows an affinity bio- and chemical sensor 40 for processing multiple sample transducers 380 (See FIG. 4) using the method of the present invention. Sensor 40 comprises a transducer array 413 that comprises an array of transducer elements 380 and a corresponding metal film layer 390 (not shown) for each element to makeup the transducer array 413. The beam reflects off this array and retains the phase and intensity information for each element 380. A beam splitter 440 is used to combine the projections of the s- and p-polarization components which are then detected by detectors 415 and 414. Detectors 414 and 415 comprise a photodetector array or a CCD camera. The detectors 414 and 415 are used to obtain an "image difference" using a differential signal analysis tool using techniques similar to the ones described above. The "image difference" contains phase information for each of the transducer elements 380 in array 413.

Figure 5:
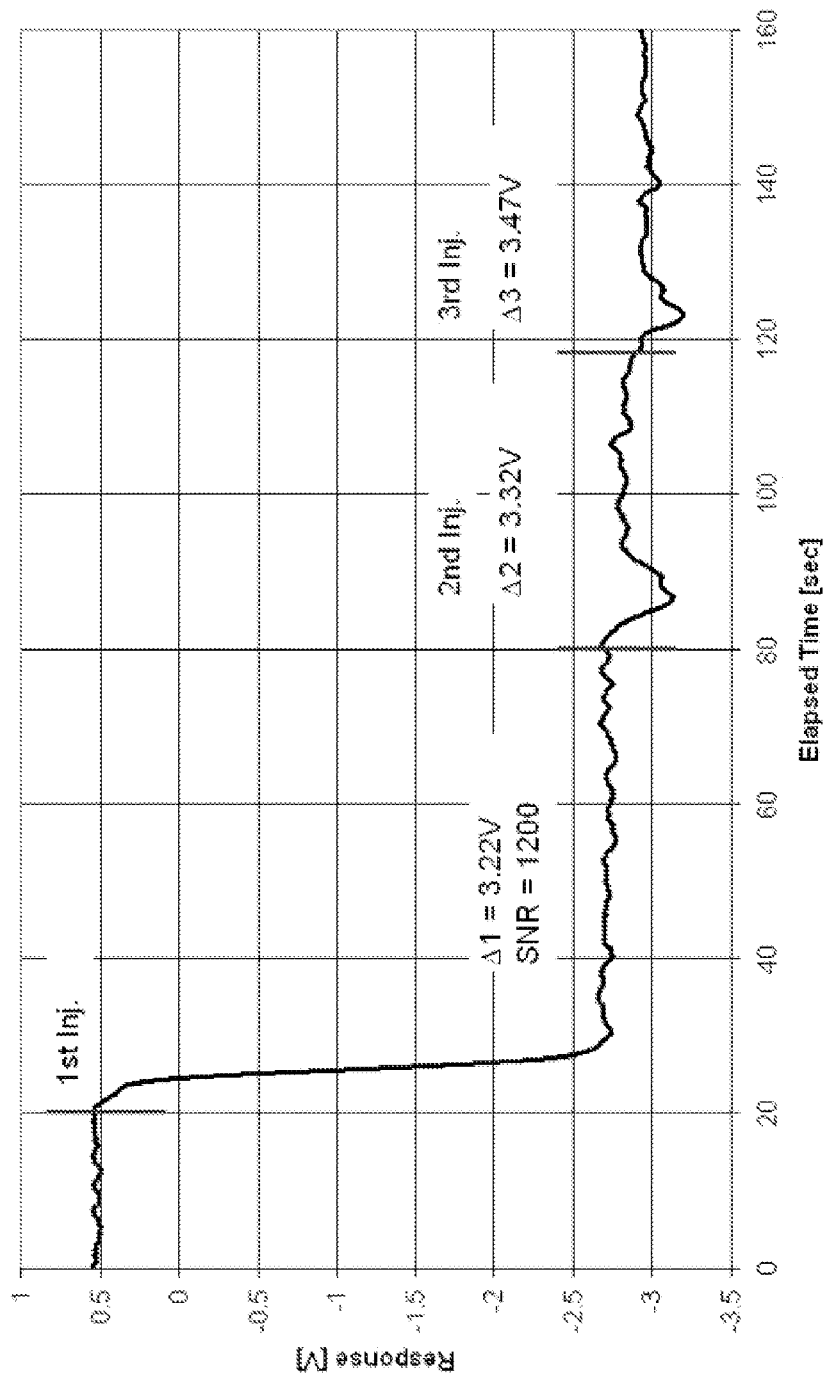
FIG. 5 illustrates a typical response of the system as a bio-affinity sensor.

FIG. 5 shows test results for a sample analyzed using a device embodying the present inventions. Three consecutive injections of 120 µL of avidin solution in buffer at 0.3 mg/mL concentration are injected over the sensing surface coated with biotinated BSA. Delta Response is the difference between response resulting from binding avidin to the surface of the transducer and initial response of the system while the buffer is flowing over the transducer. Incremental increase of the Delta Response shows that the surface of the transducer was not saturated from the first injection of avidin sample and there was additional binding during consequent injections. The method also allows investigation of the rate of the reaction by varying the volume and concentration of injected analyte and the time of exposure of the sample to the surface of the transducer.

The systems and methods disclosed herein can be used for evaluation of multiple complementary chemistries in a sample or plurality of samples. The samples are preferably fluidic in nature (e.g., liquid, gas, etc.). Examples of a fluid sample that can be obtained from an animal include, but are not limited to, whole blood, serum, sweat, tears, ear flow, sputum, lymph, bone marrow suspension, urine, saliva, semen, vaginal flow, cerebrospinal fluid, brain fluid, ascites, milk, secretions of the respiratory, intestinal and genitourinary tracts, and amniotic fluid.

The samples can be analyzed to detect and/or identify particular analyte(s) in the sample based the analyte(s)' complementary chemistries. Examples of complementary chemistries include, but are not limited to, antibody-antigen interactions, including sandwich antibody interactions, receptor-ligand interactions, including small molecules, peptides, and proteins, interaction with both natural and synthetic receptors, nucleic acids interrelations and other interactions between compositions, for example non-receptor mediated protein/protein, peptide, small organic molecule or inorganic molecule interactions.

For example, for analysis of antibody-antigen interactions, transducers can be composed of biofilms (e.g., sensor materials) where the biofilm is either composed with or coated with an antibody or an antigen for detection of complementary chemistry in any biological fluid such as blood, plasma, saliva, urine, bile, etc. or other media mix. The above can be used to detect, for example, a polypeptide or protein in a sample by using a transducer composed of biofilm(s) with an antibody that specifically binds the polypeptide or protein of interest. Useful applications of such embodiments include infectious disease diagnostics including blood supply safety, medical diagnostics, personalized medicine such as characterization and diagnosis of cancer, bio/chemical hazard or bio/chemical weapons detection, including detection of protein- and small molecule-based toxins and poisons, and immunological research. For any of these broader applications, the instrument would be employed for detection of viral or disease-related antigens, host immunoglobulins, viral particles and/or bacteria.

Compared to enzyme linked immunosorbent assays, (ELISA) the proposed system offers distinct benefits that include a much quicker time to results since incubation with additional reporter antibodies and activation enzymes is eliminated, and real time monitoring, as well as significant reduction of complexity in terms of assay process. Reduction of background signal due to non-specific binding of complex mixtures such as blood, a simple step that is similar to the blocking process used for ELISA studies is proposed—such that the complex mixture absent the analyte of interest would be passed over the transducer, non-specific binding measured, and then complex mixture containing the analyte of interest is added, resulting in signal specific to the analyte of interest. Additionally, information related to the rates of association and dissociation of the analytes of interest to the binding molecules on the biosensor can be derived.

In some embodiments, the systems and methods herein can be used to detect receptor-ligand interactions. In such embodiments, a receptor or ligand is bound to the transducer surface and the binding of the ligand to it assayed. Normally such interactions are monitored using a reporter system such as colorimetric/fluorescent or radioactive labels. The methods and systems herein allow for real-time, multiplexed combinatorial chemistry screens for drug development, pharmacokinetics, biochemical kinetic studies for association and dissociation constants, quality control of industrial processes where undesirable products or side reactions may take place, monitoring completion of chemical reactions, catalysis, ion-implantation and basic chemistry research. Where precious metals are used in catalytic processes such as hydrogenation on platinum, real time analysis and evaluation of the process may be possible via direct integration of the catalytic surface as the transducer. Kinetic studies in both drug discovery and biological research can be performed by immobilizing a biological molecule of interest, an enzyme, for example, and permit the measurement of association and dissociation or processing rate of a particular small molecule or putative biological target. Synthetic receptors may also be immobilized, i.e., for example, modified porphyrins, cyclodextrins, amongst others, to detect small molecules capable of selective binding.

In some embodiments, the systems and methods herein detect and/or monitor nucleic acid (e.g., DNA) hybridization with exquisite sensitivity. This can be used, for example, to detect hybridization of a target nucleic acid sequence to a probe on an array. Analysis of nucleic acid hybridization also permits determination of viral load, and eliminates the need for a nucleic acid amplification step if sufficient numbers (hundreds of thousands) of molecules are present to register signal, as opposed to tens of billions that other systems demand. Again, the systems and methods herein allow for the real-time detection of such analytes (e.g., target nucleic acid sequences) in a sample.

Other forms of molecular target analysis that can be performed by the present invention include detection of virus particles or other particles of biological origin in building air supply systems, chemical and biological warfare agents, water and food quality, monitoring chemical contaminants in feed and waste streams or environmental life support systems and power plant emissions. Whole bacteria may also be detected as well, in either fluid or gaseous samples. Thus, the present invention relates to infectious disease screening in blood and detection of virus or bacterial particles in air, pharmacokinetic research and primary binding studies for drug development applications in addition to personalized medicine, particularly for cancer, detection of bio- and chemical warfare agents/hazards, and quality control for industrial processes.

In any of the embodiments herein, the devices can be configured to enable high throughput screening using an array of transducers having a different probe or sample at discrete sites. For instance, chips with from ten to 1000 features could be developed to analyze small nuclear polymorphisms (SNPs), or specific hereditary markers for prenatal screening, or to determine a cancer's susceptibility to various drug regimens, or evaluate the genetic nature of psychological disease, or analyze blood samples from numerous patients for infectious disease such as hepatitis C or HIV. Analysis rate depends in part on the number of discrete sites on a chip and also on the sample volume. In some embodiments, a chip is designed with more than but not limited to 10, 100, 1,000 or 10,000 discrete sites. In some embodiments, an apparatus herein analyzes up to but not limited to 120 µL of a sample in 1-2 minutes or up to but not limited to 500 µL of a sample in 2-5 minutes. Discrete sites can have samples containing, e.g., blood or other bodily fluid, water, gaseous material, etc. Each of the discrete sites can have an address such that data collected from one sample from a unique site can be associated with a particular sample (e.g., a sample collected from a patient X).

While preferred embodiments of the present invention have been shown and described herein, it will be obvious to those skilled in the art that such embodiments are provided by way of example only. Numerous variations, changes, and substitutions will now be apparent to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A detection device for detecting an optical property of a sample material, comprising:
    a prism that comprises or is adjacent to an optical interface comprising a surface configured to come in contact with said sample material;
    a light source that generates a first light beam for application to said optical interface, wherein said first light beam comprises a first polarization component and a second polarization component, and wherein said optical interface reflects said first light beam into said prism under total internal reflection conditions;
    at least one optical retarder that provides substantially circular polarization in said first light beam downstream of said optical interface;
    a polarizing beam splitter downstream of said optical interface, wherein said polarizing beam splitter splits said first light beam into a second light beam and a third light beam after said first light beam is reflected from said optical interface;
    a detector module downstream of said polarizing beam splitter, wherein said detector module accepts said second light beam and said third light beam; and
    a processor programmed to calculate a phase shift between the first and second polarization components induced by said sample material, wherein said processor calculates said phase shift based on the difference in intensities between said second light beam and said third light beam.

2. The detection device of claim 1, wherein the device is capable of evaluating multiple complementary chemistries in a sample or a plurality of samples.

3. The detection device of claim 1, wherein the device is capable of detecting label-free nucleic acid hybridization in real time.

4. The detection device of claim 1, wherein the device is capable of detecting the presence of an analyte included in said sample material in no more than 2 minutes.

5. The detection device of claim 1, wherein the device is capable of detecting at least 50 femtograms of said sample material.

6. The detection device of claim 1, wherein said detector module comprises:
   a first detector that measures the intensity of said second light beam; and
   a second detector that measures the intensity of said third light beam.

7. The detection device of claim 1, wherein said first polarization component and said second polarization component are substantially orthogonal to each other.

8. The detection device of claim 1, wherein said at least one optical retarder provides said second phase shift such that the total phase shift between said first polarization component and said second polarization component is substantially 90° before said first beam is split into said second light beam and said third light beam.

9. The detection device of claim 1, wherein the total internal reflection conditions include total internal reflection (TIR) or frustrated total internal reflection (FTIR).

10. The detection device of claim 1, wherein said optical interface is of a transducer containing a sensing material.

11. The detection device of claim 10, wherein the sensing material comprises biological molecules.

12. The detection device of claim 10, wherein said sensing material is selected from the group consisting of antibodies, antigens, oligonucleotides, proteins, enzymes, receptors, receptor ligands, organic molecules, and catalysts.

13. The detection device of claim 1, wherein said first light beam is substantially linearly polarized.

14. The detection device of claim 1, wherein said first polarization component is in a plane of incidence, and said second polarization component is normal to the plane of incidence.

15. The detection device of claim 1, wherein said detector module comprises a chip with an array of transducers having different probes or samples at discrete sites.

16. The detection device of claim 15, wherein said chip is configured to analyze single nucleotide polymorphisms (SNPs).

17. The detection device of claim 1, wherein said sample material comprises nucleic acid, viral particles, bacteria or organic molecules.

18. The detection device of claim 1, wherein the sample material is selected from the group consisting of proteins and polypeptides.

19. A method for detecting an optical property of a sample material, comprising:
   (a) generating a first light beam comprising a first linear polarization component and a second linear polarization component;
   (b) reflecting said first light beam from an optical interface comprising said sample material, wherein said first light beam is reflected under total internal reflection conditions, and wherein with the aid of at least one optical retarder, said first light beam acquires substantially circular polarization downstream of said optical interface;
   (c) splitting said first light beam into a second light beam and a third light beam after the first light beam is reflected from said optical interface;
   (d) detecting said second light beam and said third light beam; and
   (e) calculating, with the aid of a processor, a phase shift between the first and second polarization components induced by said sample material, wherein said phase shift is calculated based on the difference in intensities between said second light beam and said third light beam.

20. The method of claim 19, wherein the first light beam is a linearly polarized coherent light beam that is rotated at a predetermined angle with respect to a plane of incidence.

21. The method of claim 19, wherein the intensities of the second and the third light beams are substantially equal.

22. The method of claim 19, further comprising converting the polarization of the first light beam from substantially elliptical polarization into substantially circular polarization before splitting the first light beam into a second light beam and a third light beam.

23. The method of claim 19, wherein the sample material comprises nucleic acid, viral particles, bacteria or organic molecules.

24. The method of claim 19, wherein said optical interface is of a transducer containing a sensing material.

25. The method of claim 24, wherein the sensing material comprises biological molecules.

26. The method of claim 24, wherein said sensing material is selected from the group consisting of antibodies, antigens, oligonucleotides, proteins, enzymes, receptors, receptor ligands, organic molecules, and catalysts.

27. The method of claim 19, wherein the phase difference induced by the sample material is a surface refractive index change of at least $5 \times 10^{-8}$ Refractive Index Units.

28. The method of claim 19, further comprising detecting said sample material based on said phase shift.

29. The method of claim 28, wherein at least 50 femtograms of said sample material is detected.

30. The method of claim 19, wherein a phase shift occurs between said first polarization component and said second polarization component upon reflection from said optical interface.

31. The method of claim 19, further comprising comparing the phase difference induced by the sample material to a phase difference induced by a reference sample.

32. The method of claim 31, wherein the reference sample has no analyte.

33. The method of claim 31, wherein the reference sample has a known analyte.

34. The method of claim 19, wherein the first and second linear polarizations are orthogonal to each other.

35. The method of claim 19, wherein the first light beam is a linearly polarized coherent light beam that is rotated at a predetermined angle with respect to a plane of incidence.

36. The method of claim 19, wherein (d) further comprises detecting the intensity of said second light beam and the intensity of said third light beam.

37. The method of claim 19, wherein said second and third light beams are detected separately.

* * * * *